(12) United States Patent
Urano et al.

(10) Patent No.: US 8,922,764 B2
(45) Date of Patent: Dec. 30, 2014

(54) DEFECT INSPECTION METHOD AND DEFECT INSPECTION APPARATUS

(75) Inventors: Yuta Urano, Yokohama (JP); Toshifumi Honda, Yokohama (JP); Yukihiro Shibata, Fujisawa (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/976,178

(22) PCT Filed: Oct. 21, 2011

(86) PCT No.: PCT/JP2011/005899
§ 371 (c)(1),
(2), (4) Date: Jul. 17, 2013

(87) PCT Pub. No.: WO2012/090367
PCT Pub. Date: Jul. 5, 2012

(65) Prior Publication Data
US 2013/0301042 A1 Nov. 14, 2013

(30) Foreign Application Priority Data

Dec. 27, 2010 (JP) ................................ 2010-289127

(51) Int. Cl.
*G01N 21/956* (2006.01)
*G01N 21/95* (2006.01)
*G01B 11/06* (2006.01)
*G01N 21/88* (2006.01)

(52) U.S. Cl.
CPC .......... *G01N 21/956* (2013.01); *G01N 21/9501* (2013.01); *G01B 11/0608* (2013.01); *G01N 2201/1045* (2013.01); *G01N 21/95623* (2013.01); *G01N 2021/8854* (2013.01)
USPC .................. 356/237.5; 356/237.1; 356/237.2; 356/237.3; 356/237.4

(58) Field of Classification Search
CPC ............ G01N 21/956; G01N 21/9501; G01N 2201/1045; G01N 21/95623; G01N 2021/8854; G01B 11/0608
USPC .......... 356/237.1–237.5; 250/559.01, 559.04, 250/559.41, 559.45
See application file for complete search history.

(56) References Cited

U.S. PATENT DOCUMENTS 5,463,459 A 10/1995 Morioka et al.
5,818,576 A * 10/1998 Morishige et al. .......... 356/237.2
(Continued)

FOREIGN PATENT DOCUMENTS

JP 61-137050 6/1986
JP 9-304289 11/1997
(Continued)

*Primary Examiner* — Sang Nguyen
(74) *Attorney, Agent, or Firm* — Antonelli, Terry, Stout & Kraus, LLP

(57) ABSTRACT

A defect inspection method includes: illuminating an area on surface of a specimen as a test object under a specified illumination condition; scanning a specimen to translate and rotate the specimen; detecting scattering lights to separate each of scattering lights scattered in different directions from the illuminated area on the specimen into pixels to be detected according to a scan direction at the scanning a specimen and a direction approximately orthogonal to the scan direction; and processing to perform an addition process on each of scattering lights that are detected at the step and scatter approximately in the same direction from approximately the same area of the specimen, determine presence or absence of a defect based on scattering light treated by the addition process, and compute a size of the determined defect using at least one of the scattering lights corresponding to the determined defect.

12 Claims, 13 Drawing Sheets

(56) References Cited

U.S. PATENT DOCUMENTS

| | | | |
|---|---|---|---|
| 5,903,342 A | 5/1999 | Yatsugake et al. | |
| 6,608,676 B1 | 8/2003 | Zhao et al. | |
| 6,774,991 B1* | 8/2004 | Danko | 356/237.4 |
| 7,385,688 B1 | 6/2008 | Kadkly et al. | |
| 7,426,023 B2* | 9/2008 | Ohshima et al. | 356/237.2 |
| 7,675,613 B2* | 3/2010 | Nakao et al. | 356/237.2 |
| 7,710,557 B2* | 5/2010 | Oshima et al. | 356/237.5 |
| 7,719,673 B2* | 5/2010 | Oshima et al. | 356/237.4 |
| 8,477,302 B2* | 7/2013 | Urano et al. | 356/237.5 |
| 2005/0185172 A1 | 8/2005 | Ishimaru et al. | |
| 2006/0256325 A1 | 11/2006 | Mcmillan et al. | |
| 2009/0161943 A1* | 6/2009 | Yamashita et al. | 382/149 |
| 2009/0213366 A1 | 8/2009 | Nakano et al. | |
| 2009/0279081 A1* | 11/2009 | Urano et al. | 356/237.5 |
| 2012/0092656 A1* | 4/2012 | Nakao et al. | 356/237.3 |
| 2012/0133928 A1 | 5/2012 | Urano et al. | |
| 2013/0003052 A1 | 1/2013 | Nakao et al. | |

FOREIGN PATENT DOCUMENTS

| | | |
|---|---|---|
| JP | 10-340450 | 12/1998 |
| JP | 2005-24327 | 1/2005 |
| JP | 2006-201179 | 8/2006 |
| JP | 2006-330007 | 12/2006 |
| JP | 2007-327815 | 12/2007 |
| JP | 2008-14849 | 1/2008 |
| JP | 2009-236791 | 10/2009 |
| JP | 2010-197352 | 9/2010 |
| JP | 2012-32252 | 2/2012 |

* cited by examiner

OPTICAL PATH NOT BRANCHED OR SYNTHESIZED

OPTICAL PATH BRANCHED AND SYNTHESIZED

OBLIQUE-INCIDENCE ILLUMINATION
TRAVEL DIRECTION

DEFECT INSPECTION METHOD AND DEFECT INSPECTION APPARATUS

TECHNICAL FIELD

The present invention relates to a defect inspection method and a defect inspection apparatus to inspect micro defects on a specimen surface and determine and output defect types and sizes.

BACKGROUND

Production lines inspect semiconductor substrates and membrane substrates for defects on the surfaces in order to maintain and improve the product yield. Defect inspection technologies of the related art are known as Japanese Unexamined Patent Application Publication No. Hei9 (1997)-304289, Japanese Unexamined Patent Application Publication No. 2006-201179, and U.S. Patent Application Publication No. 2006/0256325. These technologies condense illuminating light on a specimen surface in an area of several tens of micrometers to detect micro defects. The technologies condense and detect scattering light from a defect and inspect an area ranging from several tens of nanometers to several micrometers for defects. The technologies rotate and translate a stage supporting a specimen (test object) so that an illuminating spot helically scans the specimen surface to inspect the entire specimen surface.

The technologies described in Japanese Unexamined Patent Application Publication No. Hei9 (1997)-304289 and Japanese Unexamined Patent Application Publication No. 2006-201179 detect a component emitted at a high angle and a component emitted at a low angle in the scattering light from a defect and categorize a defect type based on a ratio.

The technology described in Japanese Unexamined Patent Application Publication No. 2006-201179 calculates the size of a detected defect based on the intensity of scattering light from the defect.

To reduce thermal damage on a specimen, the technology described in U.S. Patent Application Publication No. 2006/0256325 controls the illuminating light power, the speed to scan an illuminating spot, or the illuminating spot size while inspecting a test surface. More specifically, the technology assumes that the thermal damage given to a specimen is found by multiplying the illumination power density to be applied and the irradiation time together. While keeping the thermal damage below a specified value, the technology varies the illuminating light power, the speed to scan an illuminating spot, or the illuminating spot size according to radial positions on the specimen being scanned.

The technology described in U.S. Pat. No. 6,608,676 inspects the entire specimen surface in a short period of time by illuminating a wide range of specimen using a long Gaussian beam in one direction and detecting an illuminated area at a time using a detector such as a CCD including multiple pixels.

The technology described in U.S. Pat. No. 7,385,688 concerns the oblique-incidence illumination and uses an aspherical lens and a diffractive optical element to shape the illuminating light so as to position multiple illuminating spots on a test surface.

The technology described in Japanese Unexamined Patent Application Publication No. 2006-330007 forms an image at a slant in a two-dimensional area on the test surface and integrates and detects a detection signal using a TDI image sensor.

SUMMARY

The defect inspection used for semiconductor manufacturing processes requires detecting a micro defect, highly accurately measuring the size of the detected defect, inspecting a specimen in a non-destructive manner (or without metamorphosing a specimen), always acquiring constant results (the number of detected defects, the defect position, size, and type) from the same specimen, and inspecting many specimens in a specified time. The scattering light acquired from a micro defect is too weak and is hardly detected due to variations caused by a photon shot noise occurring on the specimen surface from the scattering light. Increasing the illumination power per unit area or the inspection time per unit area can improve the sensitivity and the accuracy of defect size estimation based on the scattering light amount. However, increasing the illumination power per unit area causes thermal damage on the specimen surface and is therefore limited. Increasing the inspection time per unit area also increases the time needed to inspect the entire specimen surface and does not satisfy the need to inspect many specimens in a specified time.

The technologies described in Japanese Unexamined Patent Application Publication No. Hei9 (1997)-304289, Japanese Unexamined Patent Application Publication No. 2006-201179, U.S. Patent Application Publication No. 2006/0256325, U.S. Pat. No. 6,608,676, and U.S. Pat. No. 7,385,688 generate too weak a scattering light from a micro defect having the size of 20 nm or smaller. A defect signal is buried in the noise due to the scattering light occurring on the specimen surface, the detector noise, or the detection circuit noise. Micro defects cannot be detected. To avoid this, increasing the illumination power increases the specimen temperature due to the illumination light and causes thermal damage on the specimen. To avoid this, decreasing the specimen scanning speed decreases a specimen area or the number of specimens that can be inspected within a specified time. For these reasons, it has been difficult to fast detect micro defects while avoiding thermal damage.

The technologies described in U.S. Patent Application Publication No. 2006/0256325, U.S. Pat. No. 6,608,676, and U.S. Pat. No. 7,385,688 form a long illumination spot in one direction, image an illumination area on a detector including multiple pixels, and detect multiple pixels. The technologies can thereby increase the storage time and the number of addition operations to detect micro defects. However, the use of several hundreds or thousands of pixels or more greatly increases the visual field of a detection lens needed for image detection. This makes detection lens production or adjustment difficult or increases detection lens costs.

The technology described in Japanese Unexamined Patent Application Publication No. 2006-330007 performs two-dimensional detection and is capable of providing more pixels than the technology of one-dimensionally placing pixels. Helical scanning or rotational scanning suited for fast scanning circular test objects allows a defect image to move while forming an arc-like trajectory during scanning. The array of pixels placed in a grid-like pattern differs from a defect scanning trajectory. The effect of storing defect signals using pixels is unsatisfactory. The specimen surface vertical moves to vary a defect image if the detection is performed in a direction oblique to a normal line of the specimen surface. The effect of storing defect signals using pixels is unsatisfactory. Due to the above-mentioned reason, defect signals are detected across pixels. The defect position cannot be accurately detected.

To address the above-mentioned problems, the present application discloses the invention that is summarized below.

(1) There is provided a defect inspection method including the following steps. An illumination step illuminates an area on surface of a specimen as a test object under a specified illumination condition. A specimen scan step translates and rotates the specimen. A scattering light detection step separates each of scattering lights scattered in different directions from the illuminated area on the specimen into pixels to be detected according to a scan direction at the specimen scan step and a direction approximately orthogonal to the scan direction. A process step performs an addition process on each of scattering lights that are detected at the scattering light detection step and scatter approximately in the same direction from approximately the same area of the specimen, determines the presence or absence of a defect based on scattering light treated by the addition process, and computes a size of the determined defect using at least one of the scattering lights corresponding to the determined defect.

The present invention can detect scan an entire sample surface in a short time and detect micro defects.

DETAILED DESCRIPTION

Figure 1:
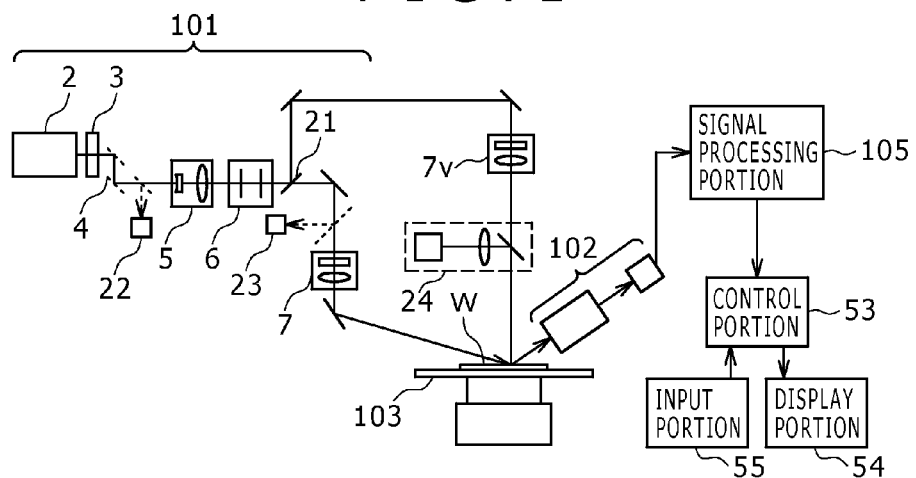
FIG. 1 is an overall schematic configuration diagram illustrating an embodiment of a defect inspection apparatus according to the invention.

FIG. 1 illustrates schematic configuration of an embodiment of the invention. The embodiment appropriately includes an illumination portion 101, a detection portion 102, a stage 103 capable of mounting specimen W, a signal processing portion 105, a control portion 53, a display portion 54, and an input portion 55.

The illumination portion 101 appropriately includes a laser beam source 2, an attenuator 3, an outgoing beam adjustment portion 4, a beam expander 5, a polarization control portion 6, and an illumination intensity distribution control portion 7.

The laser beam source 2 radiates a laser beam. The attenuator 3 adjusts the radiated laser beam to specified beam intensity. The outgoing beam adjustment portion 4 adjusts the laser beam to a specified beam position and beam travel direction. The beam expander 5 adjusts the laser beam to a specified beam diameter. The polarization control portion 6 adjusts the laser beam to a specified polarization state. The illumination intensity distribution control portion 7 adjusts the laser beam to specified intensity distribution and radiates the laser beam to a test area on specimen W.

An incidence angle of illuminating light against the specimen surface depends on the position and the angle of a reflecting mirror of the outgoing beam adjustment portion 4 provided in the optical path of the illumination portion 101. The incidence angle of the illuminating light is adjusted to be appropriate for detecting a micro defect. Increasing an illumination incidence angle or decreasing an illumination incidence angle (formed between the specimen surface and an illuminating light axis) weakens scattering light (referred to as haze) that returns from micro irregularities of the specimen surface and causes a noise to scattering light from a micro foreign matter on the specimen surface. Therefore, micro defects can be detected appropriately. It is advantageous to set the incidence angle of the illuminating light to larger than or equal to 75 degrees or set the elevation angle thereof to smaller than or equal to 15 degrees if the scattering light from micro irregularities of the specimen surface interferes with the micro defect detection. On the other hand, decreasing an illumination incidence angle for oblique-incidence illumination increases an absolute amount of scattering light from a micro foreign matter. It is advantageous to set the incidence angle of the illuminating light to larger than or equal to 60 degrees and smaller than or equal to 75 degrees or set the elevation angle thereof to larger than or equal to 15 degrees and smaller than or equal to 30 degrees if an insufficient amount of scattering light from a defect interferes with the micro defect detection. The illumination incidence angle may be variable. For oblique-incidence illumination, the polarization control portion 6 of the illumination portion 101 provides polarization control to enable the illumination polarization as P polarization. This increases the scattering light from a defect on the specimen surface compared to the other polarization states.

As illustrated in FIG. 1, a mirror 21 is inserted into an optical path of the illumination portion 101. Other mirrors are provided as needed to change the illuminating light path. The illuminating light is radiated in a direction virtually perpendicular to the specimen surface (vertical illumination). In this case, an illumination intensity distribution control portion 7v controls the illumination intensity distribution on the specimen surface similarly to the oblique-incidence illumination. The vertical illumination capable of virtually perpendicular incidence on the specimen surface is suited to a case where a beam splitter is inserted into the same position as the mirror 21 to provide oblique-incidence illumination and scattering light from a recessed defect (a polishing flaw or a crystalline defect in crystalline material) on the specimen surface. An illumination intensity distribution monitor 24 illustrated in FIG. 1 will be described later.

To detect a micro defect near the specimen surface, the laser beam source 2 oscillates an ultraviolet or vacuum ultraviolet laser beam that is predetermined as high output of 2 W or more and a short wavelength (355 nm or less) hardly penetrating into specimens. The radiated beam is approximately 1 mm in diameter. To detect defects inside specimens, the laser beam source uses a visible or infrared laser beam easily penetrating into specimens.

The attenuator 3 includes a first polarization plate, a half-wave plate rotatable around the light axis of illuminating light, and a second polarization plate. The first polarization plate converts the light incident on the attenuator 3 into linearly polarized light. The polarization direction of the linearly polarized light is rotated according to a slow axis azimuth of the half-wave plate. The linearly polarized light passes through the second polarization plate. Controlling the azimuth of the half-wave plate decreases the light intensity at any ratio. The first polarization plate may be optional if the light incident on the attenuator 3 ensures sufficiently high linear polarization. The attenuator 3 is previously calibrated in terms of the relationship between an input signal and a fading rate. The attenuator 3 may be replaced by an ND filter having concentration distribution of gradation.

The outgoing beam adjustment portion 4 includes multiple reflecting mirrors. The following describes an example of using two reflecting mirrors. However, the invention is not limited thereto. Three or more reflecting mirrors may be used. Suppose a case where a three-dimensional orthogonal coordinate system (XYZ coordinates) is defined and the light incident on the reflecting mirror travels in the positive X-direction. The first reflecting mirror is configured to deflect the incident light in the positive Y-direction (incidence and reflection in the XY plane). The second reflecting mirror is configured to deflect the light reflected off the first reflecting mirror in the positive Z-direction (incidence and reflection in the YZ plane). Moving the reflecting mirrors and adjusting tilt/swing angles of the same adjusts the position and the travel direction (angle) of the light radiated from the outgoing beam adjustment portion 4. As described above, the incidence and reflection plane (XY plane) of the first reflecting mirror is orthogonal to the incidence and reflection plane (XZ plane) of the second reflecting mirror. Therefore, the light radiated from the outgoing beam adjustment portion 4 (traveling in the positive Z-direction) can be adjusted in terms of its positions and angles in the XZ plane and the YZ plane independently.

The beam expander 5 includes two or more lens groups and increases the diameter of incident parallel light flux. The example uses a Galilean beam expander including a combination of concave and convex lenses. The beam expander 5 is provided for a translation stage having two or more axes and can be repositioned so that a specified beam position coincides with the center. The beam expander 5 has the function to adjust the tilt/swing angle of the entire beam expander 5 so that the light axis of the beam expander 5 coincides with a specified beam light axis. Adjusting the distance between lenses can control a magnification percentage of the light flux diameter (zoom mechanism). If the light incident on the beam expander 5 is not parallel, adjusting the distance between lenses simultaneously magnifies the light flux diameter and collimates the light flux (converting the light flux into substantially parallel light). To collimate the light flux, a collimation lens may be provided independently of the beam expander 5 upstream of the same. The beam expander 5 magnifies the beam diameter approximately five to 20 times. If a beam of 1 mm in diameter is radiated from the light source, the beam expander 5 magnifies the beam diameter to approximately 5 to 20 mm.

The polarization control portion 6 includes a half-wave plate and a quarter-wave plate. The polarization control portion controls the polarization state of illuminating light as requested. Beam monitors 22 and 23 are provided in the middle of the optical path for the illumination portion 101 and measure states of the light incident on the beam expander 5 and the illumination intensity distribution control portion 7.

Figure 2:
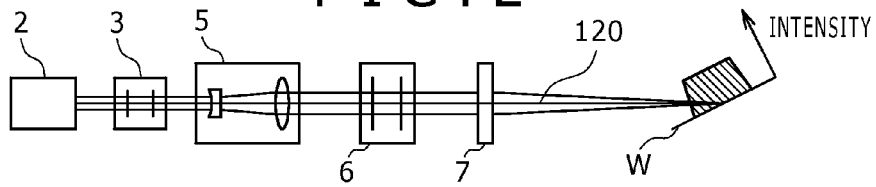
FIG. 2 illustrates a first example of an illumination intensity distribution shape provided by an illumination portion according to the invention.
Figure 3:
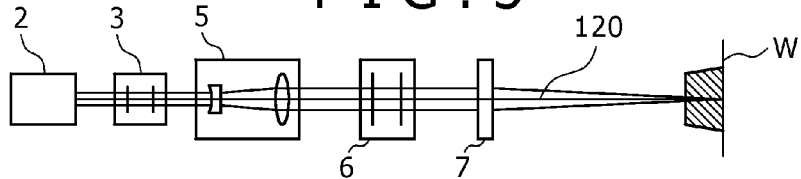
FIG. 3 illustrates a second example of an illumination intensity distribution shape provided by an illumination portion according to the invention.

FIGS. 2 and 3 illustrate illumination intensity distribution shapes provided by the illumination portion according to the invention.

FIGS. 2 and 3 illustrate positional relationship between an illuminating light axis 120 and an illumination intensity distribution shape formed by the illumination portion 101 on the specimen surface. FIGS. 2 and 3 illustrate a partial configuration of the illumination portion 101. The outgoing beam adjustment portion 4, the mirror 21, and the beam monitors 22 and 23 are omitted.

FIG. 2 schematically illustrates a sectional view of an incidence plane (including the illuminating light axis and the normal line of the specimen surface) for oblique-incidence illumination. The oblique-incidence illumination tilts in the incidence plane against the specimen surface. The illumination portion 101 generates the substantially uniform illumination intensity distribution in the incidence plane. Part of the incidence plane with uniform illumination intensity is 100 micrometers to several millimeters long in order to inspect a wide area per unit time.

FIG. 3 schematically illustrates a sectional view of a plane that includes the normal line of the specimen surface and is perpendicular to the incidence plane. Also in this plane, the illumination portion 101 generates the uniform illumination intensity distribution on the specimen surface. The illumination intensity distribution is 100 micrometers to several millimeters long. The illumination intensity distribution control portion 7 includes optical elements such as an aspherical lens, a diffractive optical element, a cylindrical lens array, and a light pipe to be described later. As illustrated in FIGS. 2 and 3, the optical elements configuring the illumination intensity distribution control portion 7 are provided perpendicularly to the illuminating light axis.

Figure 7:
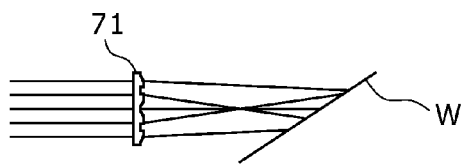
FIG. 7 illustrates a first example of an optical element provided for an illumination intensity distribution control portion according to the invention.

FIG. 7 illustrates a first example of an optical element provided for an illumination intensity distribution control portion according to the invention.

The illumination intensity distribution control portion 7 (FIG. 7) includes optical elements acting on phase distribution and intensity distribution of the incident light. The illumination intensity distribution control portion 7 uses a diffractive optical element (DOE) 71 as a constituent optical element. The diffractive optical element 71 uses a substrate made of a material that transmits the incident light. The surface of the substrate has a wavy shape finer than or equal to the wavelength of the light. Fused silica is used as a material to transmit ultraviolet incident light. The diffractive optical element 71 may be preferably coated with an antireflection film to prevent the light from attenuating due to transmission through the diffractive optical element 71. The lithography is used to form the fine wavy shape. The light passes through the beam expander 5 to transform into substantially parallel light. The substantially parallel light then passes through the diffractive optical element 71 to form the illumination intensity distribution on the specimen surface according to the wavy shape of the diffractive optical element 71. The wavy shape of the diffractive optical element 71 is designed and fabricated based on computation using the Fourier optics theory so that the illumination intensity distribution formed on the specimen surface is uniform in the incidence plane. An optical element provided for the illumination intensity distribution control portion 7 includes a translation adjustment mechanism having two or more axes and a rotation adjustment mechanism having two or more axes to be able to adjust positions and angles relative to the light axis of the incident light. In addition, a focus adjustment mechanism is provided based on movement in the light axis direction.

Figure 4:
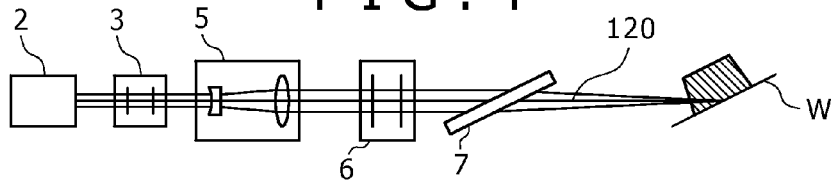
FIG. 4 illustrates a third example of an illumination intensity distribution shape provided by an illumination portion according to the invention.

FIG. 4 illustrates another modification of the illumination intensity distribution control portion 7. The modification provides an optical element configuring the illumination intensity distribution control portion 7 in parallel with the specimen surface. The optical element provided in this manner requires the ability to condense out-of-axis light that greatly tilts against the normal line for the optical element surface. On the other hand, the light is easily condensed because a constant distance is maintained between the optical element surface and the specimen surface.

Figure 14:
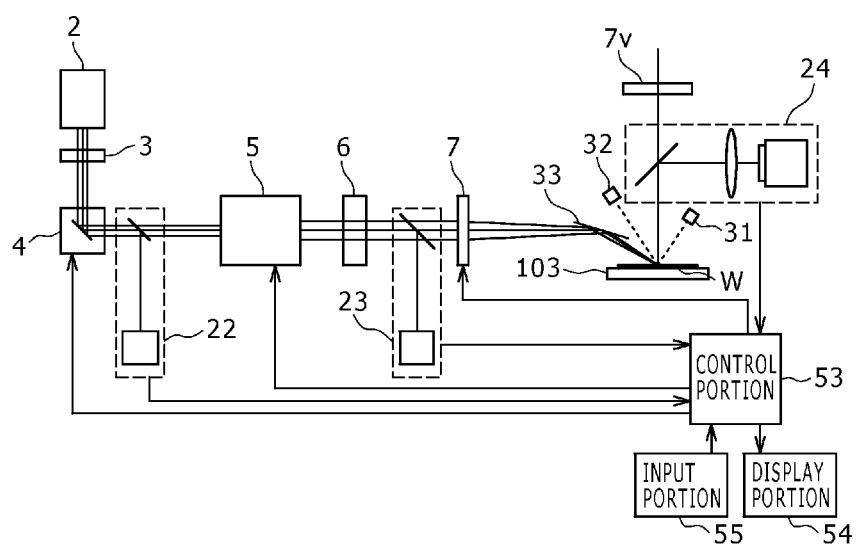
FIG. 14 illustrates a first example of a unit to measure and adjust illuminating light in the illumination portion according to the invention.

FIG. 14 illustrates a first example of a unit to measure and adjust illuminating light in the illumination portion according to the invention.

With reference to FIG. 14, the following describes a unit to measure illuminating light states in the illumination portion 101. The beam monitor 22 measures and outputs a position and an angle (travel direction) of the illuminating light passing through the outgoing beam adjustment portion 4. The beam monitor 23 measures and outputs a position and a wavefront of the illuminating light incident on the illumination intensity distribution control portion 7.

The beam monitor 22 measures a barycentric position of the illuminating light intensity to measure the illuminating light position. Specifically, the position measurement unit represents a position sensitive detector (PSD) or an image sensor such as a CCD or CMOS sensor. The beam monitor 22 measures an illuminating light angle using a position sensitive detector or an image sensor provided at a position farther from the light source than the position measurement unit. Alternatively, the beam monitor 22 measures an angle by allowing the illuminating light to enter a collimator lens. A position sensitive detector or an image sensor is placed at the focus position of the collimator lens to measure a condensed illuminating light position. The illuminating light position and the illuminating light angle measured in the beam monitor 22 are input to the control portion 53 and are displayed on the display portion 54. The outgoing beam adjustment portion 4 adjusts the illuminating light to a specified position or angle if the illuminating light deviates from the specified position or angle.

The beam monitor 23 measures illuminating light positions using a unit similar to the position measurement unit in the beam monitor 22. The beam diameter is magnified to several millimeters or more at a measurement position for the beam monitor 23. Therefore, the beam monitor 23 measures positions by reducing and projecting the measurement position as needed onto a light receiving surface of the position measurement unit such as a position sensitive detector. To measure parallelism of the light incident on the illumination intensity distribution control portion 7, a shearing interferometer or a Shack-Hartmann wavefront sensor measures the illuminating light. The shearing interferometer measures divergence and convergence states of the illuminating light. To do this, an optical glass approximately several millimeters thick is slantwise inserted into the illuminating light path. Both surfaces of the optical glass are polished flat. The shearing interferometer applies the illuminating light to both surfaces of the optical glass and projects reflected light from both surfaces onto a screen to observe an interference pattern. A representative example is SPUV-25 manufactured by SIGMA KOKI Co., LTD. Installing an image sensor such as a CCD or CMOS sensor at the screen position enables to automatically measure divergence and convergence states of the illuminating light. The Shack-Hartmann wavefront sensor divides a wavefront using a fine lens array, projects the divided wavefronts to an image sensor such as a CCD sensor, and varies projection positions to measure wavefront tilts. Compared to the shearing interferometer, the Shack-Hartmann wavefront sensor can measure wavefronts in detail such as partial wavefront disturbance. The wavefront measurement may reveal that diverged or converged light, not substantially parallel light, enters the illumination intensity distribution control portion 7. In such a case, moving the lens group of the preceding beam expander 5 in the light axis direction can approximate the illuminating light to substantially parallel light.

Figure 15:
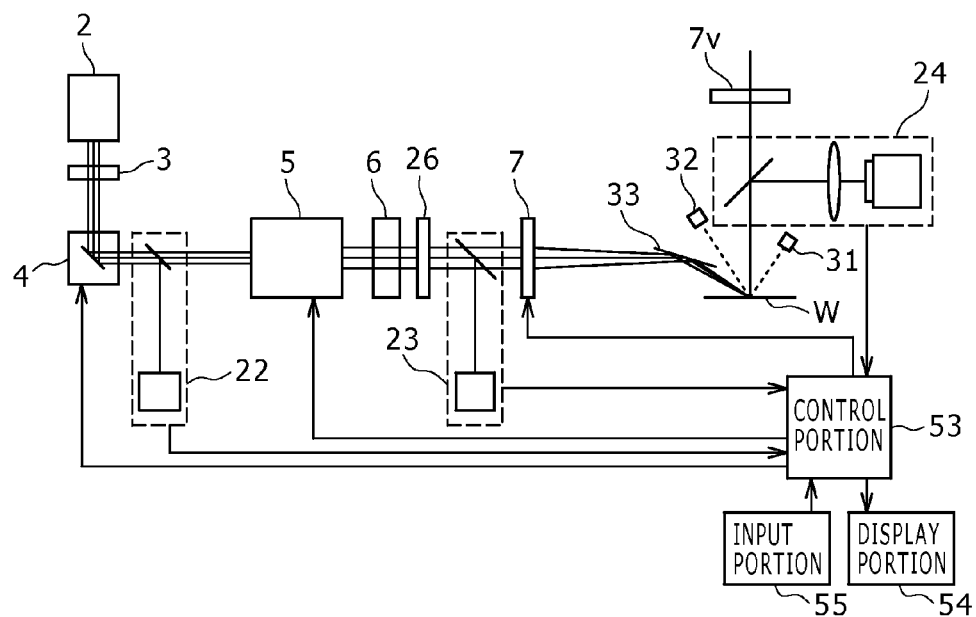
FIG. 15 illustrates a second example of a unit to measure and adjust illuminating light in the illumination portion according to the invention.

FIG. 15 illustrates a second example of a unit to measure and adjust illuminating light in the illumination portion according to the invention. The wavefront measurement may reveal a partially tilted wavefront of the light incident on the illumination intensity distribution control portion 7. In such a case, a spatial light phase modulator 26 as a type of spatial light modulator (SLM) is inserted to precede the illumination intensity distribution control portion 7 as illustrated in FIG. 15. The spatial light phase modulator 26 supplies each light flux section position with an appropriate phase difference to flatten the wavefront. This enables the wavefront to approximate to be flat, namely, the illuminating light to approximate to substantially parallel light. The above-mentioned unit to measure and adjust the wavefront accuracy can restrict a wavefront accuracy (variation from a specified wavefront (design value)) of the light incident on the illumination intensity distribution control portion 7 to $\lambda/10$ rms or less.

The illumination intensity distribution monitor 24 measures illumination intensity distribution on the specimen surface adjusted in the illumination intensity distribution control portion 7. The illumination intensity distribution monitor 24 similarly measures illumination intensity distribution on the specimen surface adjusted in the illumination intensity distribution control portion 7v if the vertical illumination is used as illustrated in FIG. 1. The illumination intensity distribution monitor 24 images the specimen surface on an image sensor such as a CCD or CMOS sensor via a lens and detects the specimen surface as an image. The control portion 53 processes an illumination intensity distribution image detected in the illumination intensity distribution monitor 24 to compute the barycentric position of the intensity, the maximum intensity, the maximum intensity position, and the width and length of the illumination intensity distribution. The width and length corresponds to an illumination intensity distribution region that satisfies a specified intensity or more or a specified ratio or more against the maximum intensity value. The display portion 54 displays these computation results as well as a contour shape and a sectional waveform of the illumination intensity distribution.

The oblique-incidence illumination varies the specimen surface height to disturb the illumination intensity distribution due to variation and defocus of the illumination intensity distribution position. To solve this problem, the specimen surface height is measured. A height variation, if any, is corrected using the illumination intensity distribution control portion 7 or the height adjustment according to the Z axis of the state 103. The specimen surface height measurement uses a beam emission portion 31 and a light receiving portion 32 to receive a beam that is emitted from the beam emission portion 31 and is diffused and reflected off the specimen surface. The beam emission portion 31 includes a light source such as semiconductor laser and a projection lens. The light receiving portion 32 includes a light receiving lens and a position sensitive detector. The beam emission portion 31 and the light receiving portion 32 measure highly glossy specimen surfaces such as semiconductor silicon surfaces and magnetic disk substrate surfaces. The beam emission portion 31 and the light receiving portion 32 are provided so that the beam emission portion 31 emits light and the light receiving portion 32 detects the light specularly reflected off the specimen surface. A position sensitive detector of the light receiving portion 32 detects a variation in the specimen surface height as a position gap between light spots based on the triangulation principle.

A deflection unit 33 adjusts a deflection angle to correct a position gap along in-plane direction of the specimen at the position of radiated illuminating light. The deflection unit 33 is provided downstream of the illumination intensity distribution control portion 7 and directs the illuminating light to the specimen surface. The deflection unit 33 includes a reflecting mirror to deflect the illuminating light and a piezoelectric element to control the tilt/swing angle against the illuminating light axis of the reflecting mirror. The deflection unit 33 controls the tilt/swing angle within a range of approximately ±1 mrad at a frequency of 400 Hz or more. The measured height variation and the incidence angle of the illuminating light are used to find a position gap amount along in-plane direction of the specimen at the position of radiated illuminating light. To correct this gap, the deflection unit 33 receives a control signal output from the control portion 53 and controls the reflecting mirror. The illumination intensity distribution monitor 24 may directly measure the barycentric position of the illumination intensity distribution to correct a position gap along in-plane direction of the specimen at the position of radiated illuminating light. Suppose a case where the deflection unit 33 corrects a position gap due to a variation of the specimen surface height along in-plane direction of the specimen at the position of radiated illuminating light. In this case, the optical path length between the illumination intensity distribution control portion 7 and the specimen surface varies from the length before the correction. The illuminating spot may be defocused depending on variations. A variation in the optical path length is found from the measured height variation and the incidence angle of the illuminating light. Based on the variation, the optical element provided for the illumination intensity distribution control portion 7 is repositioned in the light axis direction or the divergence angle of beam expander 5 is adjusted to reduce the defocus.

If the light source 2 uses a pulse laser easily capable of high output, illumination energy given to the specimen concentrates on the moment the pulse is applied. A momentary temperature rise due to the applied pulse may cause a thermal damage to the specimen.

Figure 17:
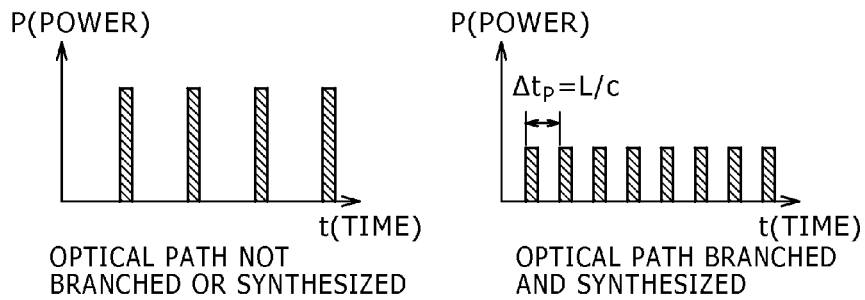
FIG. 17 illustrates results of energy reduction per pulse according to optical path branch and synthesis.

FIG. 17 illustrates results of energy reduction per pulse according to optical path branch and synthesis. To avoid a thermal damage to the specimen due to the applied pulse, it is effective to reduce the energy per pulse while maintaining the total energy as illustrated in FIG. 17. To do this, the optical path for pulse laser is branched. An optical path difference is provided between branched optical paths. After that, the optical paths are synthesized.

Figure 16:
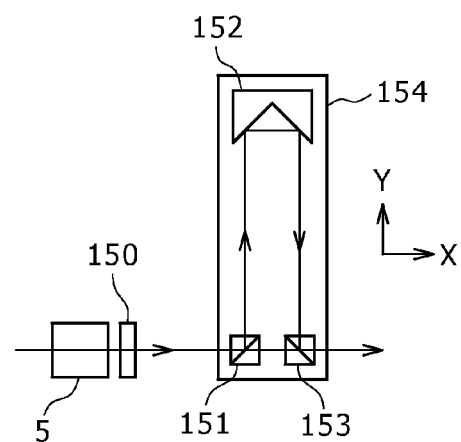
FIG. 16 illustrates a first example of a unit to reduce the energy per pulse by branching and synthesizing optical paths in the illumination portion according to the invention.

FIG. 16 illustrates a first example of a unit to reduce the energy per pulse by branching and synthesizing optical paths in the illumination portion according to the invention.

A polarization beam splitter 151 branches the illuminating light passing through the beam expander 5 into first and second optical paths. The first optical path reflects off the polarization beam splitter 151. The second optical path passes through the polarization beam splitter 151. The first optical path reflects off a retroreflector 152 to return, reflects off a polarization beam splitter 153, and is synthesized with the second optical path. The retroreflector 152 includes two or more reflecting mirrors orthogonal to each other and returns the input light 180 degrees in the opposite direction. It is necessary to equalize the intensity of the light reflecting off the polarization beam splitter 151 with that of the light passing through the same. To do this, a wave plate 150 adjusts the illuminating light polarization to circularly polarized light or 45-degree slantwise linearly polarized light. Assume L to be an optical path difference between the first optical path and the second optical path. Then, time interval $\Delta tp = L/c$ is found between a light pulse passing through the first optical path and a light pulse passing through the second optical path. Suppose that $\Delta tp$ is set to be greater than or equal to the time required to alleviate a temperature rise due to an applied pulse. This can prevent a momentary temperature rise in the specimen due to a single pulse and a temperature rise resulting from heat storage due to multiple pulses.

Two mirrors independent of each other may be used to return the first optical path. In this case, a relative angle difference between the two mirrors, if any, causes an angle difference between two light fluxes to be synthesized. However, the retroreflector 152 causes no angle difference. As illustrated in FIG. 16, the illumination portion 101 including the optical system is mounted on an aluminum optical plate, for example. An environmental change such as a temperature change may distort the optical plate. Distortion of the optical plate may change the position of the retroreflector 152 in the X-direction as illustrated in FIG. 16 with reference to the light flux input to the retroreflector 152. In such a case, the light flux may reflect on the retroreflector 152, return to the polarization beam splitter 153, change the light flux position to the X-direction, and cause a position gap. To solve this problem, the polarization beam splitters 151 and 153 and the retroreflector 152 are mounted on a plate 154 that is mounted on the optical plate supporting the illumination portion 101. This can maintain the relative positional relationship regardless of effects such as distortion due to the layout or shape of the entire optical plate supporting the illumination portion 101. The plate 154 using a low-expansion material such as glass ceramics can effectively suppress distortion due to a temperature change.

Figure 18:
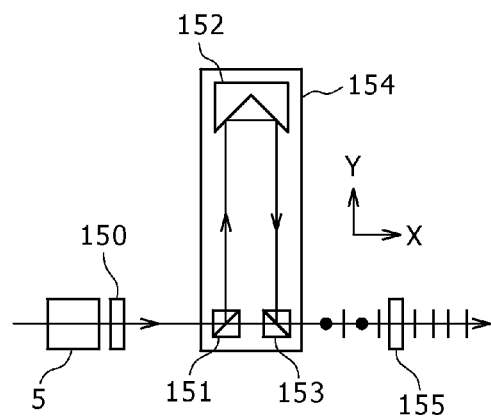
FIG. 18 illustrates a second example of a unit to reduce the energy per pulse by branching and synthesizing optical paths in the illumination portion according to the invention.

With reference to FIG. 18, the following describes a modification of the example that branches and synthesizes optical paths as illustrated in FIG. 16. If the optical path is branched and synthesized as illustrated in FIG. 16, synthesizing two optical paths results in no polarization because the polarization components overlap in two directions without interfering with each other. The subsequent polarization control portion 6 is subject to an illumination energy loss in generating the linearly polarized light. A solution to this problem is to use a polarization-modulating element 155 capable of temporarily changing polarization states of the transmitted light. The polarization-modulating element 155 can align all pulse polarization states and generate the linearly polarized light without illumination energy loss. The polarization-modulating element 155 represents a photoelastic modulator (PEM), a liquid crystal element, an electrooptic modulator, and an acousto-optic modulator.

Figure 19:
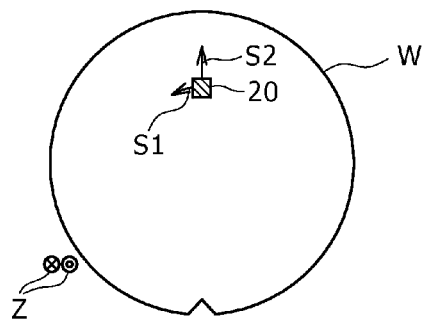
FIG. 19 illustrates an illumination distribution shape and scan directions on a specimen surface according to the invention.
Figure 20:
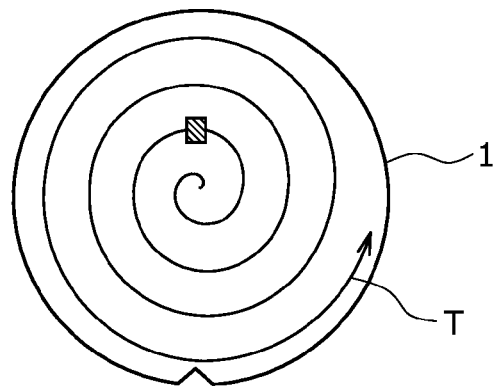
FIG. 20 illustrates a trajectory formed by an illuminating spot for scanning.

With reference to FIGS. 19 and 20, the following describes an illuminance distribution shape (illuminating spot 20) formed by the illumination portion 101 on the specimen surface and a specimen scan method. FIG. 19 illustrates an illumination distribution shape and scan directions on the specimen surface according to the invention. FIG. 20 illustrates a trajectory formed by an illuminating spot for scanning.

Specimen W is assumed to be a circular semiconductor silicon wafer. The stage 103 includes a translation stage, a rotation stage, and a Z stage (none of these shown) to adjust the specimen surface height. As described above, the illuminating spot 20 has a rectangular illumination intensity distribution. A direction S2 is assumed to be orthogonal to one side. A direction S1 is assumed to be orthogonal to the direction S2. Rotational movement of the rotation stage enables scanning in the circumferential direction S1 around the rotation axis of the rotation stage. Translational movement of the translation stage enables scanning in the translation direction S2 of the translation stage. While scanning in the scan direction S1 allows the specimen to rotate one revolution, scanning in the scan direction S2 travels a distance shorter than or equal to the length of the illuminating spot 20 in a longitudinal direction. The illuminating spot forms spiral trajectory T on specimen W to scan the entire surface of the specimen 1.

As illustrated in FIG. 20, the spiral scan allows an effective scan speed to approximate to zero at the center of the specimen surface. The illuminating light is radiated for a long time. The temperature rises to the maximum at the center of the entire specimen surface. The attenuator 3 in the illumination portion 101 controls the illumination power according to illuminating spot scanning speeds, making it possible to ensure the maximum scattering light amount without damaging specimens.

Figure 21:
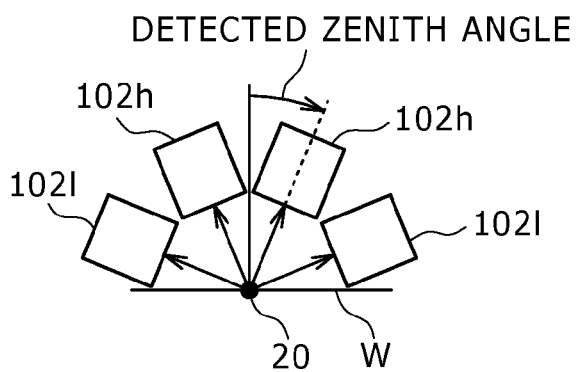
FIG. 21 is a side view illustrating placement and detection directions of a detection portion according to the invention.
Figure 22:
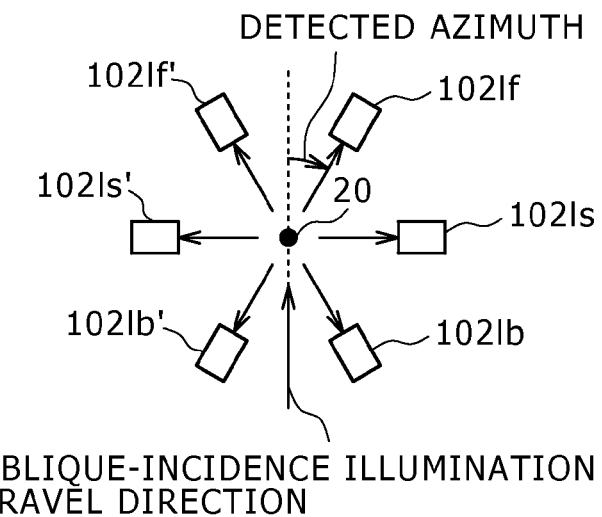
FIG. 22 is a top view illustrating placement and detection directions of a low-angle detection portion according to the invention.
Figure 23:
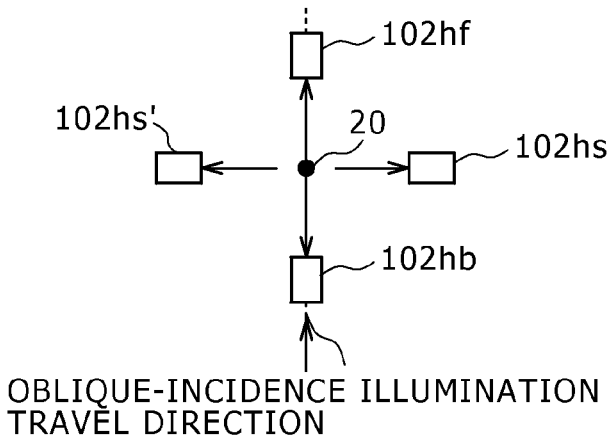
FIG. 23 is a top view illustrating placement and detection directions of a high-angle detection portion according to the invention.

Multiple detection portions 102 are provided to detect the scattering light from the illuminating spot 20 in multiple directions. With reference to FIGS. 21 through 23, the following describes examples of placing the detection portions 102 in relation to specimen W and the illuminating spot 20. FIG. 21 is a side view illustrating placement and detection directions of a detection portion according to the invention. FIG. 22 is a top view illustrating placement and detection directions of a low-angle detection portion according to the invention. FIG. 23 is a top view illustrating placement and detection directions of a high-angle detection portion according to the invention.

FIG. 21 is a side view illustrating the placement of a detection portion 102. A detected zenith angle is defined between the normal line of specimen W and the detection direction (toward the center of a detection aperture) of the detection portion 102. The detection portion 102 includes a high-angle detection portion 102*h* and a low-angle detection portion 102*l*. The high-angle detection portion 102*h* forms the detected zenith angle of 45 degrees or less. The low-angle detection portion 102*l* forms the detected zenith angle of 45 degrees or more. Multiple high-angle detection portions 102*h* and low-angle detection portions 102*l* are provided to cover the scattering light that scatters in many directions at the corresponding detected zenith angles.

FIG. 22 is a top view illustrating the placement of the low-angle detection portion 102*l*. A detection azimuth is defined between the travel direction and the detection direction for the oblique-incidence illumination within a plane parallel to the surface of specimen W. The low-angle detection portion 102 includes a low-angle forward detection portion 102*lf*, a low-angle side detection portion 102*ls*, a low-angle backward detection portion 102*lb*, a low-angle forward detection portion 102*lf'*, a low-angle side detection portion 102*ls'*, and a low-angle backward detection portion 102*lb'* as needed. The low-angle forward detection portion 102*lf'*, the low-angle side detection portion 102*ls'*, and the low-angle backward detection portion 102*lb'* are symmetric with respect to illumination incidence planes of the low-angle forward detection portion 102*lf*, the low-angle side detection portion 102*ls*, and the low-angle backward detection portion 102*lb*, respectively. For example, the low-angle forward detection portion 102*lf* is placed to maintain the detection azimuth 0 degrees or more and 60 degrees or less. The low-angle side detection portion 102*ls* is placed to maintain the detection azimuth 60 degrees or more and 120 degrees or less. The low-angle backward detection portion 102*lb* is placed to maintain the detection azimuth 120 degrees or more and 180 degrees or less.

FIG. 23 is a top view illustrating the placement of the high-angle detection portion 102*h*. The high-angle detection portion 102 includes a high-angle forward detection portion 102*hf*, a high-angle side detection portion 102*hs*, a high-angle backward detection portion 102*hb*, a high-angle side detection portion 102*hs*, and a high-angle side detection portion 102*hs'* as needed. The high-angle side detection portion 102*hs'* is symmetric with respect to an illumination incidence plane of the high-angle side detection portion 102*hs*. For example, the high-angle forward detection portion 102*hf* is placed to maintain the detection azimuth 0 degrees or more and 45 degrees or less. The high-angle side detection portion 102*s* is placed to maintain the detection azimuth 45 degrees or more and 135 degrees or less. The high-angle backward detection portion 102*b* is placed to maintain the detection azimuth 135 degrees or more and 180 degrees or less. The example uses four high-angle detection portions 102*h* and six low-angle detection portions 102*l*. However, the invention is not limited thereto. The number of detection portions and positions of the same may be changed as needed.

Figure 24:
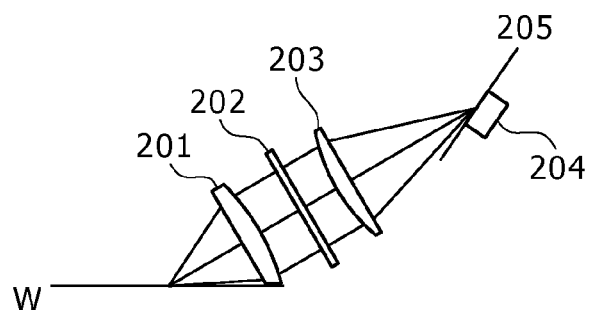
FIG. 24 illustrates a first example configuration of a detection portion according to the invention.
Figure 25:
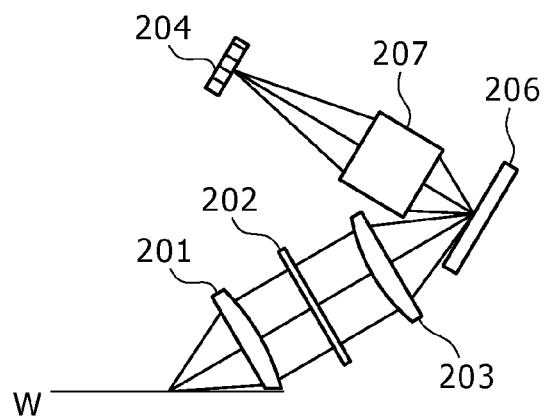
FIG. 25 illustrates a second example configuration of a detection portion according to the invention.

Specific configurations of the detection portion 102 are illustrated in FIGS. 24 and 25. FIG. 24 illustrates a first example configuration of the detection portion.

An objective lens 201 condenses scattering light from the illuminating spot 20. The scattering light passes through a polarization filter 202. An imaging lens 203 guides the scattering light to the light receiving surface of a multi-pixel sensor 204 to detect the scattering light. The objective lens 201 advantageously ensures a detection NA of 0.3 or more to efficiently detect the scattering light. For low-angle detection portions, the bottom end of the objective lens 201 is cut as needed to prevent the bottom end of the same from interfering with specimen surface W. The polarization filter 202 includes a polarization plate or a polarization beam splitter. The polarization filter 202 is provided to remove linearly polarized light components in any directions. The polarization plate represents a wire grid polarization plate with transmissivity of 80% or more, for example. The polarization filter 202 may be configured to include a wave plate and a polarization plate to remove any polarization components including oval polarization.

The multi-pixel sensor 204 includes linearly arranged light detection pixels. For highly sensitive detection, the multi-pixel sensor 204 is preferably capable of high quantum efficiency (30% or more) and electrically amplifying electrons after photoelectric conversion. For high-speed processing, the multi-pixel sensor 204 is preferably capable of allowing the light detection pixels to read signals in parallel. For ensuring a dynamic detection range, the multi-pixel sensor 204 is preferably capable of easily changing the detection sensitivity (electric amplification gain) using an electric unit in a short time. Optical detectors to satisfy these conditions are capable of electrically amplifying electrons after photoelectric conversion and include a multi-anode photomultiplier, an avalanche photodiode array, an Electron Multiplying CCD (EM-CCD), an Electron Bombardment CCD (EBCCD), an Electron Bombardment CMOS (EBCMOS), and a low-noise CMOS-Active Pixel Sensor (CMOS-APS). The objective lens 201 and the imaging lens 203 form a specimen surface image on a specimen surface conjugate plane 205. An image plane tilts against the light axis because the lens system tilting against the specimen surface forms images. The relationship between an object surface and the image plane is found according to the Scheimpflug principle. The light receiving surface of the multi-pixel sensor 204 is configured in conformity to the tilted image plane so that the tilted image plane does not cause defocus. The scattering light to be detected enters from a direction tilting against the normal line for the light receiving surface of the multi-pixel sensor 204. Preferably, the light receiving surface is coated to increase the incidence angle transmissivity.

FIG. 25 illustrates a modified example configuration of the detection portion 102. The objective lens 201 condenses scattering light from the illuminating spot 20. The scattering light passes through the polarization filter 202. The imaging lens 203 forms a specimen surface image (intermediate image) on a diffraction grating 206 provided for a plane conjugate to the specimen surface. An imaging system 207 projects the specimen surface image formed on the diffraction grating 206 onto the light receiving surface of the multi-pixel sensor 204 to detect the specimen surface image. The multi-pixel sensor 204 is provided in a plane conjugate to the specimen surface in conformity to the unidirectionally long shape of the illuminating spot 20 so that the pixel arrangement direction corresponds to the longitudinal direction of an image at the illuminating spot 20. When the imaging lens 203 guides the light that forms an intermediate image, the diffraction grating 206 diffracts that light in the normal line direction on the surface of the diffraction grating 206. The diffraction grating 206 is shaped so that nth-order diffraction light for the incident light travels along the light axis of the light guided by the imaging lens 203 to form an intermediate image and is directed toward the normal line for the surface of the diffraction grating 206. First-order diffraction light (N=1 or −1) favorably improves the diffraction efficiency. A blazed diffraction grating is used to improve the diffraction efficiency. The multi-pixel sensor 204 is provided for the plane conjugate to the specimen surface according to the above-mentioned configuration. An effective visual field can be ensured across a wide range also in the S1 direction on the specimen surface while suppressing the defocus. The detection can reduce a loss in the light intensity because the scattering light perpendicularly enters the light receiving surface of the multi-pixel sensor 204.

Even defects of the same size vary the wave height of a scattering light signal if the illumination power is controlled according to illuminating spot scanning speeds. The illumination power control is provided in parallel with control over an applied voltage that determines the electron multiplication gain for the multi-pixel sensor 204 of the detection portion 102. A dynamic range of the multi-pixel sensor 204 dynamically corresponds to the illumination power control. The applied voltage is controlled so that the electron multiplication gain for the multi-pixel sensor 204 is inversely proportional to the illumination power density of the illuminating spot, that is, the illumination power applied at each of the illuminating spot scanning speeds.

The following describes relationship among the size of the illuminating spot 20, the optical magnification of the detection portion 102, and the size of the multi-pixel sensor 204. For highly sensitive and high-speed inspection, the illuminating spot 20 is set to approximately 1 mm long. The multi-pixel sensor 204 may use a CCD or CMOS image sensor containing 256×256 pixels arranged at a 10 μm interval. In such a case, the detection portion enables the optical magnification of 2.56. The pixels are projected onto the specimen surface at a 3.9 μm interval. Under this condition, rotating the specimen at the rotation rate of 2000 rpm scans the entire surface of a circular specimen 300 mm in diameter in 4.5 seconds and scans the entire surface of a circular specimen 450 mm in diameter in 6.8 seconds. For more highly sensitive inspection, the illuminating spot is redundantly scanned in a radial direction of the specimen during revolution before and after the rotational scanning. During one revolution of the specimen, the scan distance in the R direction is set to equal 1/M multiplied by the length of the illuminating spot in the R direction. The scan area for the illuminating spot partially overlaps with an area scanned by the illuminating spot during the most recent revolution. As a result, locations on the specimen are scanned M times. Adding a signal to detect the same location M times improves the sensitivity by √M times compared to the above-mentioned scan condition. Under the scan condition, the entire surface of the specimen 300 mm in diameter is scanned in 6.4, 9.0, 13, and 18 seconds when M is set to 2, 4, 8, and 16, respectively.

Figure 26:
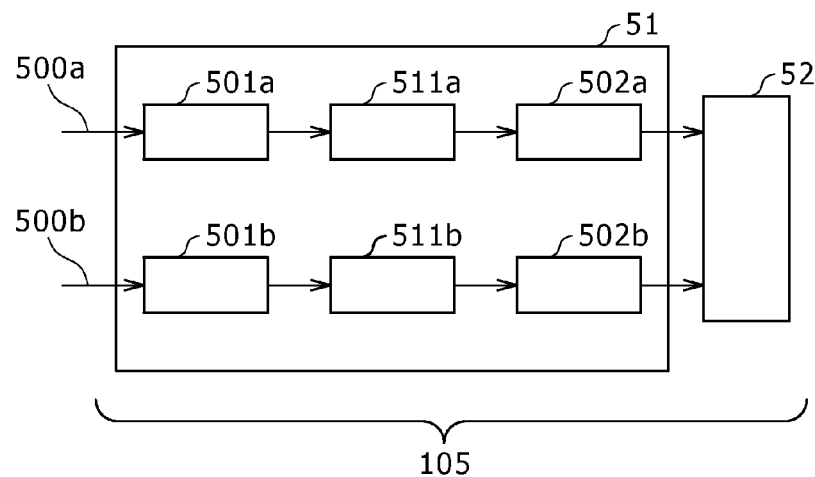
FIG. 26 illustrates configuration of an analog processing portion according to the invention.
Figure 27:
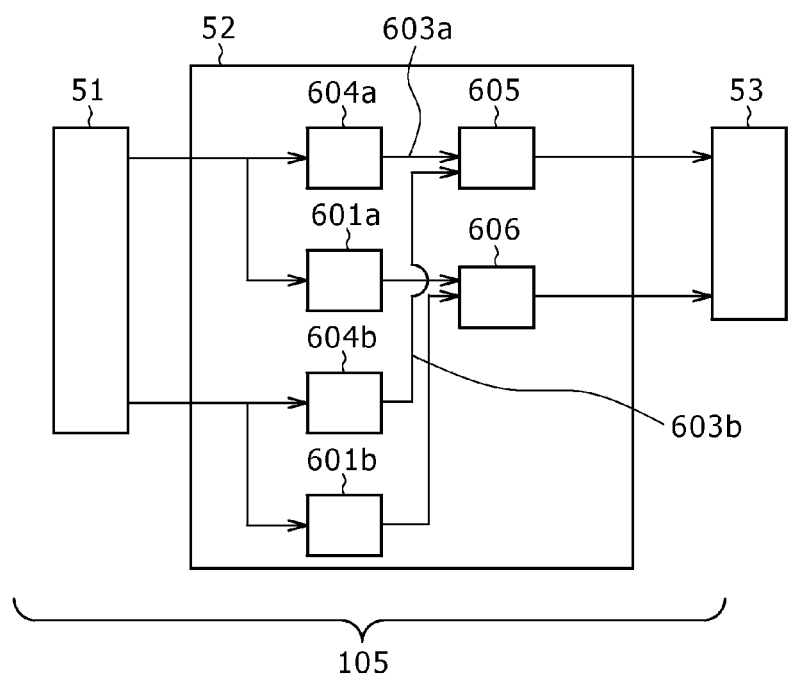
FIG. 27 illustrates configuration of a digital processing portion according to the invention.

With reference to FIGS. 26 and 27, the following describes the signal processing portion 105 that highly accurately categorizes various defect types and estimates defect sizes based on a scattering light intensity detection signal in various directions simultaneously detected by multiple optical detection systems covering a wide angular range. The signal processing portion 105 includes an analog processing portion 51 and a digital processing portion 52.

With reference to FIG. 26, the following describes the analog processing portion 51 included in the signal processing portion 105. For simplicity, the description concerns the configuration of the analog processing portion 51 including two detection portions 102a and 102b (not shown) out of the detection portions 102. Detectors provided for the detection portions 102a and 102b output signal currents 500a and 500b. Pre-amplifier portions 501a and 501b convert the signal currents into voltages to be amplified. Low-pass filters 511a and 511b remove high-frequency noise components from the amplified analog signals. Analog-digital conversion portions (A/D conversion portions) 502a and 502b convert the analog signals into digital signals to be output. The A/D conversion portions 502a and 502b feature sampling rates higher than cutoff frequencies of the low-pass filters 511a and 511b.

The above-mentioned configuration is applicable to the analog processing portion 51 when the multi-pixel sensor 204 uses a current-output sensor such as a multi-anode photomultiplier or an avalanche photodiode array. The pre-amplifier portions 501a and 501b are unneeded when the multi-pixel sensor 204 uses a CCD image sensor such as EMCCD or EBCCD or a CMOS image sensor such as EBCMOS or CMOS-APS. This is because the signal is output as a voltage. The analog processing portion 51 is unneeded if the image sensor itself includes the A/D conversion function. A digital signal output from the image sensor just needs to be input to the digital processing portion 52.

To improve the detection accuracy, the multi-pixel sensor 204 including two-dimensionally arrayed pixels detects an image on the specimen surface and adds a signal that detects the same location on the specimen more than once. Normal straightforward scanning uses a time-delay integration (TDI) CCD or CMOS image sensor. A detected signal charge is vertically transferred in synchronization with the scanning speed. As a result, a signal for the same location can be repeatedly detected for the number of times corresponding to the number of vertical transfer stages.

Figure 28:
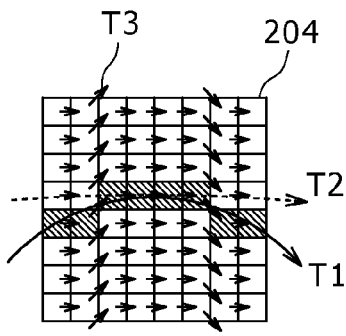
FIG. 28 illustrates relationship between a specimen scan trajectory and an array of pixels in a multi-pixel sensor according to the invention.

The embodiment performs rotational scanning suitable for high-speed inspection on circular specimens. An image at the same location on the specimen moves to draw arcs (T1 and T2) on the light receiving surface of the multi-pixel sensor 204 (FIG. 28). FIG. 28 illustrates relationship between a specimen scan trajectory and an array of pixels in the multi-pixel sensor according to the invention.

Scanning an outer periphery of the specimen increases the curvature radius for an image trajectory. An electric charge just needs to be transferred similarly to normal TDI image sensors. Scanning an inner periphery of the specimen decreases the curvature radius for an image trajectory. The trajectory extends over pixels on multiple rows in the vertical direction in FIG. 28. Similarly to normal TDI image sensors, suppose a case of transferring signal charges in the horizontal direction (corresponding to the circumferential direction of the specimen) as illustrated in FIG. 28. In such a case, a detection signal at the defect position captures a detection signal (noise) at a position other than the defect. The detection sensitivity degrades. To solve this problem, the signal transfer is shifted in the vertical direction (radial direction of the specimen) as illustrated with arrow group T3 in FIG. 28. As a result, a signal enters shaded pixels corresponding to trajectory T1 of the image and is added, making the highly sensitive detection available. The curvature radius of the image trajectory varies with scan positions in the radial direction of the specimen. A combination of additional pixels needs to be changed according to scan positions in the radial direction of the specimen. With reference to FIG. 28, the image trajectory movement speed in the horizontal direction is variable if the image trajectory has a small curvature radius. The vertical signal transfer rate is also changed according to the trajectory movement speed in the horizontal direction. A combination of signal addition pixels and the vertical transfer rate can be varied as described above if the multi-pixel sensor 204 uses a detector capable of simultaneously reading signals for all pixels in parallel such as a multi-anode photomultiplier or an avalanche photodiode array or a CMOS-TDI image sensor capable of reading and processing high-speed parallel signals.

Figure 29:
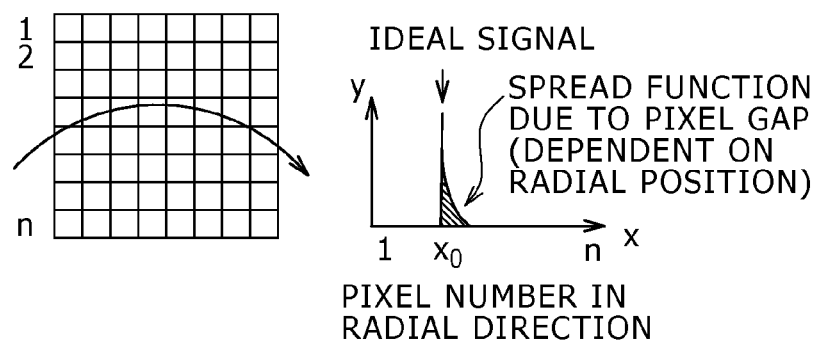
FIG. 29 illustrates spread of a defect signal due to rotational scanning according to the invention.

If the above-mentioned addition does not change the combination, the defect detection signal extends across multiple pixels in the radial direction of the specimen and indicates the spread (FIG. 29). FIG. 29 illustrates spread of a defect signal due to rotational scanning according to the invention. The following equation 1 finds the spread according to the radial direction.

$$y = \frac{1}{\sqrt{\left(\frac{R}{R-x+x_0}\right)^2 - 1}} \qquad \text{[Equation 1]}$$

In equation 1, R denotes the scan position in the radial direction of the specimen and $x_0$ denotes the original defect position without the signal spread. This relational expression is used to perform a process to recover an ideal signal without spread. As a result, it is possible to prevent the sensitivity degradation due to a decrease in the signal peak value and reduce a detection error at the defect position in the radial direction. Specifically, the digital processing portion 52 to be described later performs convolution or deconvolution for spread function profiles using equation 1 on a profile for the defect signal having the spread in the radial direction.

With reference to FIG. 27, the following describes the digital processing portion 52 included in the signal processing portion 105. In the digital processing portion 52, high-pass filters 604a and 604b respectively extract defect signals 603a and 603b from output signals from the analog processing portion 51. The defect signals are input to a defect determination portion 605. Defects locally exist on the specimen surface. A defect signal is output instantaneously in a short time and contains high-frequency components in terms of frequency bands. The high-pass filters 604a and 604b filter high frequency bands containing defect signal waveforms to remove low frequency bands and direct-current components that contain relatively much noise. This improves S/N ratios of the defect signals 603a and 603b. The high-pass filters 604a and 604b are each available as a high-pass filter or a bandpass filter designed to pass a specific cutoff frequency and eliminate components higher than or equal to the frequency as well as an FIR filter similar to the shape of the illuminating spot 20. The high-pass filters 604a and 604b output signals containing defect waveforms. The defect determination portion 605 processes these signals using threshold values and determines whether a defect is found. The defect determination portion 605 is supplied with defect signals based on detection signals from multiple optical systems. The defect determination portion 605 processes the sum of defect signals or a weighted average thereof using threshold values. Alternatively, the defect determination portion 605 applies an OR or AND operation to defects extracted from the process performed on the defect signals using threshold values in the same coordinate system provided for the wafer surface. The highly sensitive defect inspection is available compared to the defect detection based on a single defect signal.

The defect determination portion 605 supplies the control portion 53 with defect information about a location determined to indicate the presence of a defect. The defect information is output to the display portion 54. The defect information includes defect coordinates indicating the defect position in the wafer and an estimated value of the defect size computed based on the defect waveform and the sensitivity information signal. The defect coordinates are computed with reference to the gravity center of the defect waveform. The defect size is computed based on an integrated value or the maximum value for the defect waveform.

Output signals from the analog processing portion 51 are input to the high-pass filters 604a and 604b included in the digital processing portion 52 as well as the low-pass filters 601a and 601b. The low-pass filters 601a and 601b output low frequency components and direct-current components corresponding to the scattering light amount (haze) from micro roughness at the illuminating spot 20 on the wafer. Output from the low-pass filters 601a and 601b is input to a haze processing portion 606 to process haze information. The haze processing portion 606 outputs a haze signal, i.e., a signal corresponding to the haze magnitude at each location on the wafer from the magnitude of input signals acquired from the low-pass filters 601a and 601b. Angular distribution of the scattering light amount from the roughness varies with the spatial frequency distribution of micro roughnesses. As illustrated in FIGS. 21 through 23, the haze processing portion 606 is supplied with haze signals from the detectors of the detection portions 102 provided according to different orientations and angles. The haze processing portion 606 can provide information about the spatial frequency distribution of micro roughnesses according to their intensity ratios.

Figure 8:
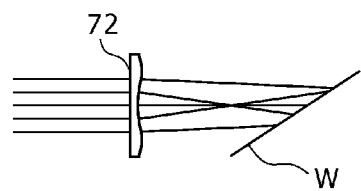
FIG. 8 illustrates a second example of an optical element provided for an illumination intensity distribution control portion according to the invention.
Figure 12:
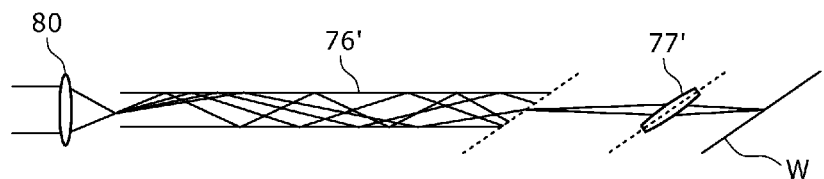
FIG. 12 illustrates a sixth example of an optical element provided for an illumination intensity distribution control portion according to the invention.
Figure 13:
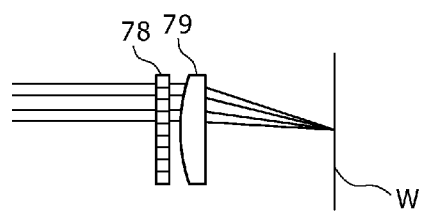
FIG. 13 illustrates a seventh example of an optical element provided for an illumination intensity distribution control portion according to the invention.

The following describes a modified example of optical elements used for the illumination intensity distribution control portion 7. Alternative optical elements having functions comparable to the diffractive optical element 71 include a spherical lens, an aspherical lens 72 (FIG. 8), a combination of a cylindrical lens array 74 and a cylindrical lens 75 (FIGS. 9 and 10), a combination of a light pipe 76 and an imaging lens 77 (FIGS. 11 and 12), and a spatial light modulator (SLM) 78 (FIG. 13).

The spherical lens is used to provide Gaussian distribution illumination that illuminates an area wider than the area detected by the detection portion 102. As a demerit, the illumination power density at the end of the detection area is lower than that at the center thereof. As a merit, the spherical lens is less sensitive to a variation in input light than the diffractive optical element. The spherical lens can provide stable illuminance distribution.

Figure 9:
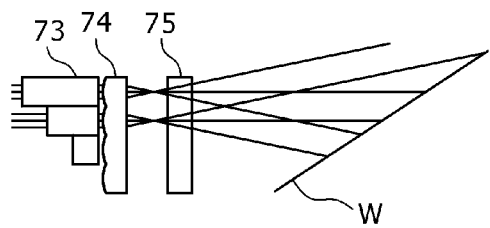
FIG. 9 illustrates a third example of an optical element provided for an illumination intensity distribution control portion according to the invention.
Figure 10:
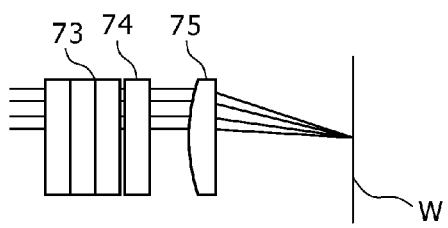
FIG. 10 illustrates a fourth example of an optical element provided for an illumination intensity distribution control portion according to the invention.

As illustrated in FIG. 9, the cylindrical lens array 74 separates the incident parallel light flux into multiple parallel light fluxes, bends them in an illumination incident plane against the specimen surface, and superposes them each other on the specimen surface while shifting their positions. If the light source 2 uses a laser beam source, superposing illuminating light fluxes on the specimen surface causes a speckle and degrades the uniformity of the illumination intensity distribution. To avoid this problem, a step-like optical path difference provision unit 73 made of a silica glass block generates an optical path difference longer than the coherence length for the light source between illuminating light fluxes. As illustrated in FIG. 10, an incident light flux passes as parallel light through the cylindrical lens array 74 in the illumination incident plane against the specimen surface. The cylindrical lens 75 condenses the light flux on the specimen surface. The light pipe 76 is a circular or rectangular cylinder. An inner wall of the light pipe 76 is made of metal or a similar material that reflects the illuminating light at a high reflectivity. The inside of the light pipe 76 is hollow or is filled with a material that transmits the illuminating light at a high transmission. A condenser lens 80 precedes the light pipe 76 and condenses the light near an entry of the light pipe 76. The light is repeatedly reflected while passing through the inside of the light pipe 76. The light indicates the spatially uniform intensity distribution at an exit of the light pipe 76. The imaging lens 77 allows the exit of the light pipe 76 to be conjugate to the specimen surface. The light intensity distribution formed on the specimen surface is similar to the uniform light intensity distribution at the exit of the light pipe 76.

Figure 11:
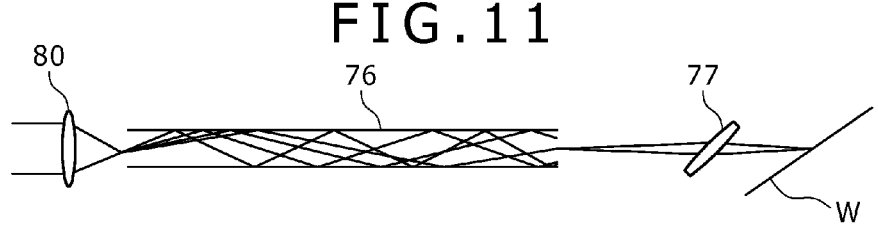
FIG. 11 illustrates a fifth example of an optical element provided for an illumination intensity distribution control portion according to the invention.

As illustrated in FIG. 11, the imaging lens 77 is tilted against the exit surface of the light pipe 76 and the light axis. The imaging lens 77 can thereby form an image of uniform illumination intensity distribution on specimen surface W. Alternatively, as illustrated in FIG. 12, a light pipe 76' is fabricated so that its exit surface is parallel to specimen surface W. An imaging lens 77' can be easily designed because the optical path distance remains constant between the light pipe exit surface and the specimen surface regardless of image heights. The spatial light modulator 78 in FIG. 13 controls the illumination intensity distribution on the specimen surface by modulating the intensity or the phase of each micro region in the section of the incident light flux. The spatial light modulator 78 receives a control signal from the control portion 53 and is capable of dynamically controlling the illumination intensity distribution on the specimen surface. The spatial light modulator 78 is available as a liquid crystal element, a magnetooptic spatial light modulator, or a digital micro-mirror device (reflection type). The spatial light modulator 78 alone or a combination of the spatial light modulator 78 and a condenser lens 79 forms the illumination intensity distribution as requested.

Figure 30:
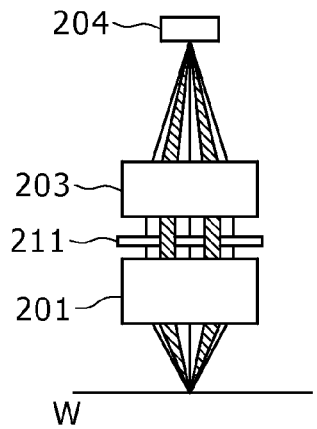
FIG. 30 illustrates a third example configuration of a detection portion according to the invention.

FIG. 30 illustrates a modified example of the detection portion 102 that collects the light scattering to tilt against the normal line of the specimen surface and detects a formed image. The objective lens 201 condenses the scattering light from the illuminating spot 20. The light passes through the polarization filter 202 (omitted in FIG. 30). The imaging lens 203 guides the light to the light receiving surface of the multi-pixel sensor 204 to detect the light. A spatial filter 211 is provided at the pupil position of the objective lens 201. The spatial filter 211 partially blocks and partially transmits the light flux passing through the pupil to be able to transmit only scattering light components in a specified scattering direction. Changing the shape of the spatial filter 211 or choosing from spatial filters with different shapes makes it possible to select a range to transmit the light flux and select a direction of the scattering light to be detected. Even if the specimen surface moves vertically, the configuration prevents an image position gap in the image plane while a defocus occurs. However, the configuration increases the cost because it requires an objective lens with relatively large NA.

Figure 31:
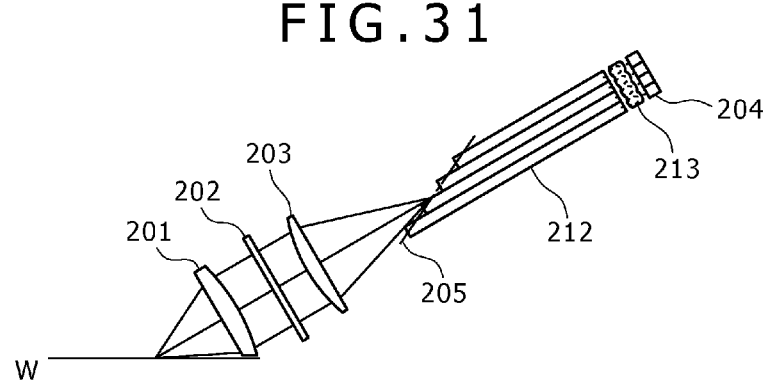
FIG. 31 illustrates a fourth example configuration of a detection portion according to the invention.

FIG. 31 illustrates another modified example of the detection portion 102 that collects the light scattering to tilt against the normal line of the specimen surface and detects a formed image. Similarly to the embodiments illustrated in FIGS. 24 and 25, the objective lens 201 condenses the scattering light from the illuminating spot 20. The light passes through the polarization filter 202. The imaging lens 203 forms the specimen surface conjugate plane 205. The specimen surface conjugate plane 205 is provided with an entrance to an optical fiber bundle 212. In addition, the incidence direction of the optical fiber bundle 205 is aligned to light axes of the objective lens 201 and the imaging lens 203. The light thereby enters the optical fiber bundle 205. A microlens array 213 couples an exit of the optical fiber bundle 205 with the light receiving surface of the multi-pixel sensor 204. The multi-pixel sensor 204 can thereby detect an image on the specimen surface conjugate plane 205.

Figure 32:
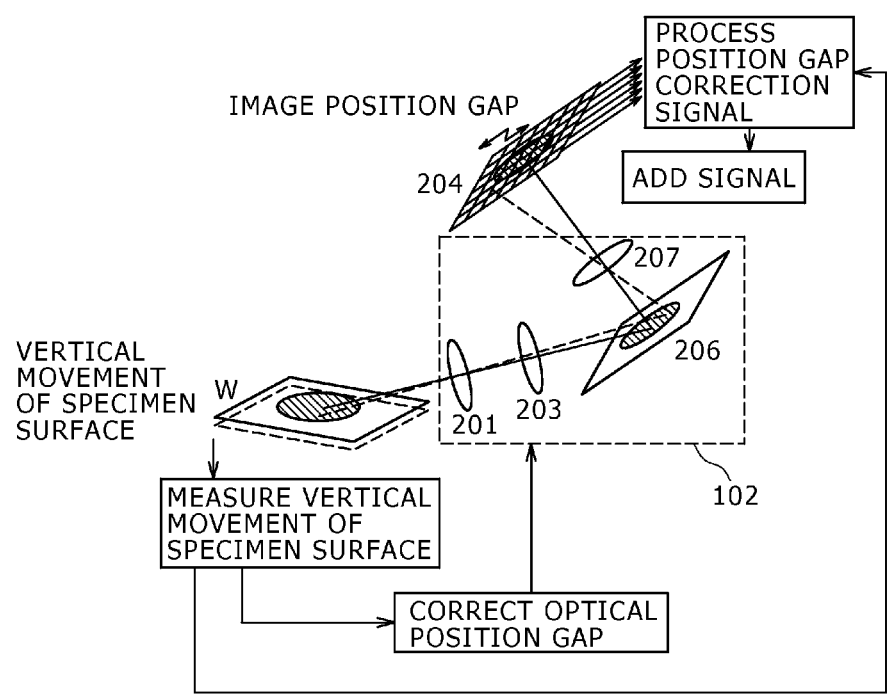
FIG. 32 illustrates an image position gap due to vertical movement of a specimen and a related correction method according to the invention.

With reference to FIG. 32, the following describes a method of adding signals corresponding to vertical movement of the specimen surface. FIG. 32 illustrates an image position gap due to vertical movement of a specimen and a related correction method according to the invention.

Scanning the specimen surface causes the specimen surface to finely move vertically in relation to the detection portion 102 due to the scanning accuracy or the specimen holding accuracy of the stage 13 or the surface accuracy of the specimen surface. If the detection portion 102 is configured as illustrated in FIG. 24, 25, or 31, vertical movement of the specimen surface changes a defect position on the specimen in a direction perpendicular to the image plane (defocus) and in the image plane (position gap). No problem occurs if the defocus falls within a focal depth of the detection portion 102. However, the position gap of an image affects misalignment of defect detection positions. If the same location is detected more than once to add signals as described above, detection signals are added at different locations instead of the same location. This may degrade the sensitivity. Solutions to these problems include optical position gap correction corresponding to vertical movement of the specimen surface and a position gap correction signal process.

Figure 33:
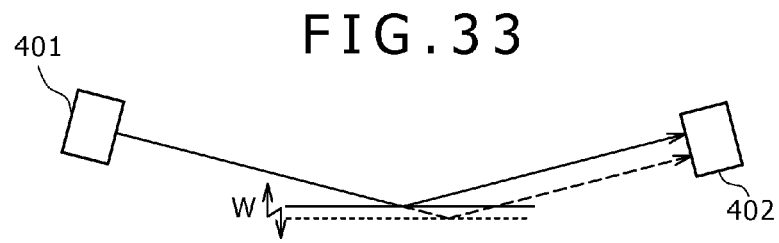
FIG. 33 illustrates a unit to measure height variations on a specimen surface according to the invention.

FIG. 33 illustrates a configuration of an optical system that measures vertical movement of the specimen surface. A light source 401 radiates a light beam for vertical movement measurement. The light beam reflects near a position to be inspected on the specimen surface and enters a position detector 402. The position detector 402 includes a photodiode or a CCD sensor and is capable of detecting a micro position gap for the incident light beam. Though omitted in FIG. 33, a projector lens is favorably inserted between the specimen surface and the position detector 402 so as to project an image at the radiated position on the specimen surface onto the position detector 402. The purpose is to eliminate an effect of angle misalignment on the specimen surface.

Figure 34:
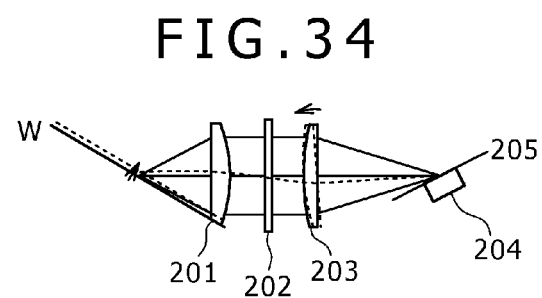
FIG. 34 illustrates optical position gap correction in a detection portion according to the invention.

FIG. 34 illustrates an embodiment of the optical position gap correction. An angle between the imaging lens 203 of the detection portion 102 and the light axis is changed to cancel an image position gap found from a result of measuring changes on the specimen surface. This can optically decrease the position gap. This can be also done by changing an angle between the objective lens 201 and the light axis. Angles of some lenses may be changed if a combination of lenses configures the imaging lens 203 or the objective lens 201. The position of a multi-pixel detector, not lenses, may be changed in a direction parallel to the image plane to cancel an effect of the image position gap. According to the configuration using the diffraction grating as illustrated in FIG. 25, the position of the diffraction grating 206 may be changed to cancel an effect of the image position gap. The optical position gap correction can reduce the defocus by moving the lens or the sensor in the light axis direction based on results of measuring the specimen surface height.

Figure 35:
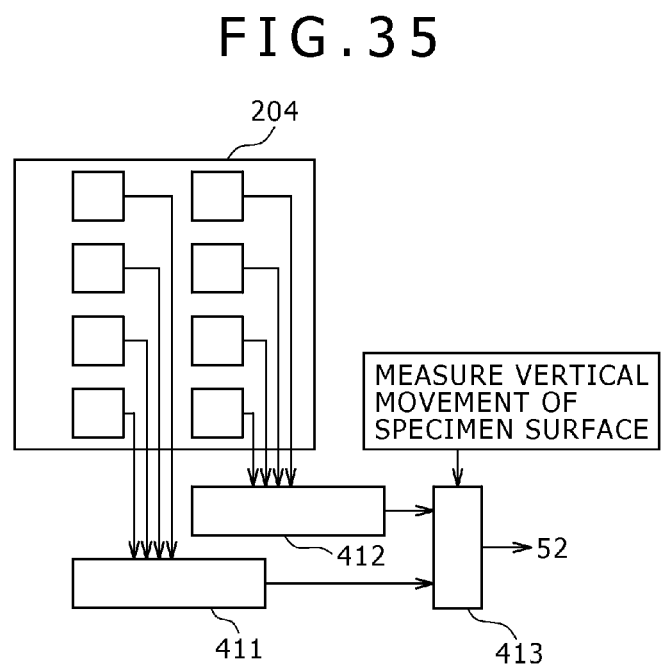
FIG. 35 illustrates configuration of a signal addition portion according to the invention.

With reference to FIG. 35, the following describes a position gap correction signal process method corresponding to vertical movement of the specimen surface. FIG. 35 illustrates configuration of a signal addition portion according to the invention.

The multi-pixel sensor 204 is assumed to have a function of digitally outputting signals for pixels. If the multi-pixel sensor 204 does not have the digital signal output function, digital signals are output by passing output signals from the multi-pixel sensor 204 to the analog processing portion 51 not shown in FIG. 35. Memory portions 411 and 412 temporarily store signals for pixels. The signal addition portion 413 aligns signals stored in the memory portions 411 and 412 so as to add signals together at the same location on the specimen surface. After the alignment, the signal addition portion 413 performs an addition process. A position gap amount as the alignment reference is computed based on the geometric position relation and imaging conditions for the detection portion 102 resulting from measurements for vertical movement of the specimen surface as illustrated in FIG. 33.

Figure 5:
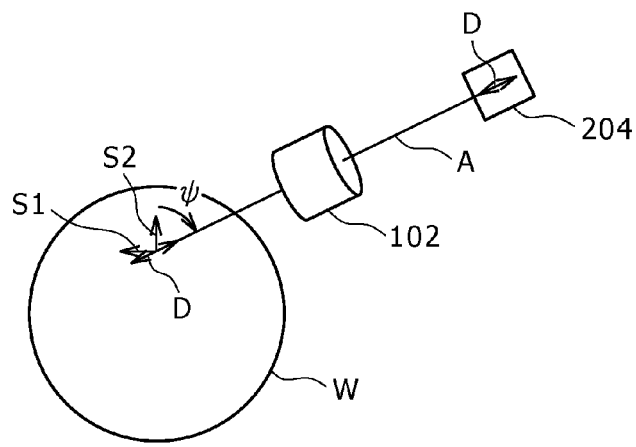
FIG. 5 illustrates an image position gap direction due to vertical movement on a specimen surface according to the invention.
Figure 6:
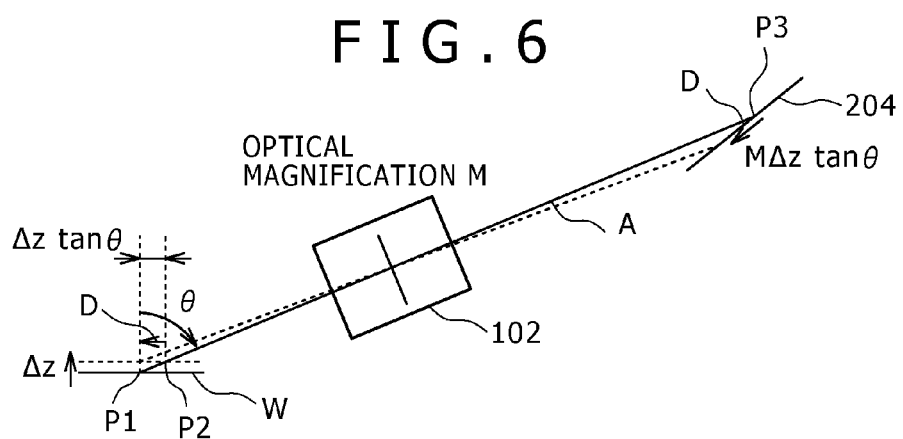
FIG. 6 illustrates the amount of image position gap due to vertical movement on a specimen surface according to the invention.

FIGS. 5 and 6 illustrate a method of computing the position gap amount based on the geometric position relation and imaging conditions for the detection portion 102 resulting from measurements for vertical movement of the specimen surface as illustrated in FIG. 33. FIG. 5 is a top view illustrating the specimen surface and the detection portion 102 viewed from the top of the specimen surface. FIG. 5 illustrates relationship between the detection direction of the detection portion 102 and the direction of a position gap due to vertical movement of the specimen surface. Angle $\phi$ in FIG. 5 corresponds to the detection azimuth. If the specimen surface moves vertically as illustrated in FIG. 5, the light flux parallel to light axis A of the detection portion 102 moves in direction D parallel to a line corresponding to light axis A that is parallel projected to the specimen surface from the normal line direction of the specimen surface. Accordingly, an image position gap occurs in direction D.

FIG. 6 illustrates relationship between the amount of vertical displacement of the specimen surface and the position gap amount. The detection portion 102 is assumed to form detected zenith angle $\theta$. If no vertical movement occurs, position P1 on the specimen surface is imaged at position P3 on the multi-pixel sensor. If the specimen surface is displaced $\Delta z$ upward, the image at position P2 is formed at position P3 on the multi-pixel sensor. Position P2 is displaced $\Delta z \tan \theta$ in direction D from position P1 on the specimen surface. Original position P1 is displaced $M\Delta z \tan \theta$ (where M is the optical magnification of the detection portion 102) on the multi-pixel sensor 204. The position gap just needs to be corrected $-M\Delta z \tan \theta$ in a direction corresponding to direction D on the multi-pixel sensor 204.

Figure 36:
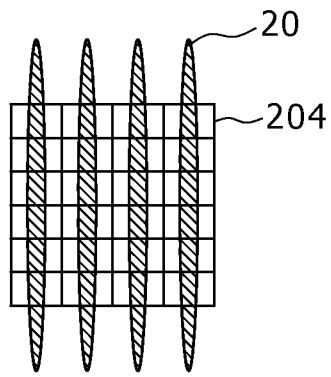
FIG. 36 illustrates relationship between illumination intensity distribution and the multi-pixel sensor according to the invention.
Figure 37:
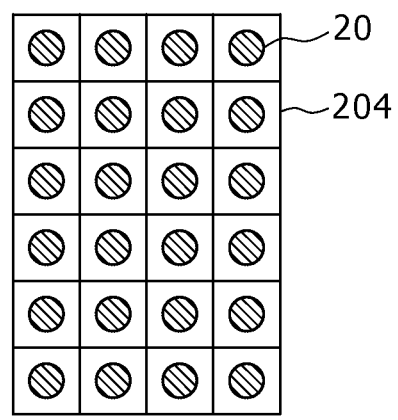
FIG. 37 illustrates relationship between illumination intensity distribution and the multi-pixel sensor according to the invention.

FIGS. 36 and 37 provide modified examples of the illumination intensity distribution to illuminate a two-dimensional area. FIGS. 36 and 37 illustrate positional relationship between the illuminating spot 20 on the specimen surface and a pixel (projected on the specimen surface) of the multi-pixel sensor 204.

FIG. 36 illustrates an example of arraying thin linear intensity distributions as the illuminating spot 20. A row of pixels corresponds to one linear light beam. An area with low illumination power density is formed between linear light beams in a transverse direction. The heat due to the illumination power is easily radiated to hardly cause damage to the specimen. High illumination power can be applied per unit area compared to illumination on the entire two-dimensional area.

FIG. 37 illustrates an example of arraying micro circular intensity distributions as the illuminating spot 20. One pixel corresponds to one circular light beam. An area with low illumination power density is formed between circular light beams in transverse and longitudinal directions. The heat due to the illumination power is easily radiated to hardly cause damage to the specimen. High illumination power can be applied per unit area compared to illumination on the entire two-dimensional area and the array of linear light beams as illustrated in FIG. 36.

Figure 38:
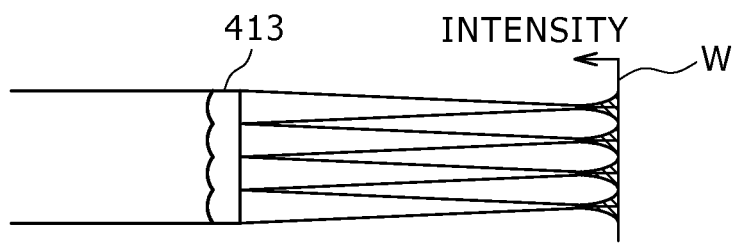
FIG. 38 illustrates configuration of the illumination intensity distribution control portion to generate multiple linear light beams according to the invention.

The cylindrical lens array 413 operates on a light beam magnified by the beam expander 5 to be able to generate the illuminating spot 20 (FIG. 38) formed by an array of linear light beams as illustrated in FIG. 36. FIG. 38 illustrates configuration of the illumination intensity distribution control portion to generate multiple linear light beams according to the invention.

A lens array including spherical lenses placed in a two-dimensional grid-like pattern operates on a light beam magnified by the beam expander 5 to be able to generate the illuminating spot 20 formed by an array of linear light beams as illustrated in FIG. 37.

As described above, one example of the invention enables the inspection using the optical placement for the oblique illumination and detection capable of highly efficiently detecting the scattering light for micro defects.

Another example of the invention illuminates a two-dimensional area on the specimen, parallel detects the illuminated area using two-dimensionally placed pixels, and stores and adds detection signals occurring substantially at the same location.

Still another example of the invention rotationally scans the specimen and configures and corrects a combination of additional pixels so that multiple pixels detect and add signals occurring substantially at the same location on the specimen.

Yet another example of the invention rotationally scans the specimen and changes combinations of additional pixels according to detection positions on the specimen so that multiple pixels detect and add signals occurring substantially at the same location on the specimen.

Still yet another example of the invention reduces the image defocus or position gap resulting from vertical movement of the specimen surface against the detection system while obliquely imaging and detecting the illuminated area. For this purpose, the example measures the vertical movement of the specimen surface and mechanically displaces the detection system or part of the optical element configuring the detection system based on measurements.

Yet still another example of the invention reduces additional pixel displacement due to the image defocus or position gap resulting from vertical movement of the specimen surface against the detection system while obliquely imaging and detecting the illuminated area. For this purpose, the example measures the vertical movement of the specimen surface and corrects a combination of additional pixels based on measurements.

The present invention can detect scan an entire sample surface in a short time, detect micro defects, and highly accurately compute the size of a detected defect.

What is claimed is:

1. A defect inspection method performed by a processing unit constructed at least in part by hardware, the defect inspection method comprising:
   an illumination step of illuminating an area on surface of a specimen as a test object under a specified illumination condition;
   a specimen scan step of translating and rotating the specimen;
   a scattering light detection step of separating each of a plurality of scattering lights scattered in a plurality of directions from the illuminated area on the specimen into a two dimensional plurality of pixels, to be detected according to both a scan direction at the specimen scan step and a direction approximately orthogonal to the scan direction; and
   a process step of performing an addition process on scattering lights that are detected by plural pixels of the two dimensional plurality of pixels corresponding to a radial direction of the specimen, determining presence or absence of a defect based on scattering light treated by the addition process, and computing a size of the determined defect using at least one of the scattering lights corresponding to the determined defect.

2. The defect inspection method according to claim 1, wherein an addition process at the process step corrects a combination of scattering lights scattering approximately in the same direction from approximately the same area of the specimen based on a displacement amount measured at the specimen surface displacement measuring step.

3. The defect inspection method according to claim 1, further comprising:
   a display step of displaying a position and a defect size detected on a surface of the specimen as determined to be defective at the process step.

4. The defect inspection method according to claim 1, wherein the specimen scan step moves the specimen by translation and rotation to spirally scan a surface of the specimen.

5. The defect inspection method according to claim 1, wherein the illumination condition includes light intensity, a beam diameter, a polarization state, and an incidence angle.

6. A defect inspection apparatus comprising:
   an illumination unit to illuminate an area on surface of a specimen as a test object under a specified illumination condition;
   a specimen scan unit to translate and rotate the specimen;
   a scattering light detection unit to separate each of a plurality of scattering lights scattered in a plurality of directions from the illuminated area on the specimen into a two dimensional plurality of pixels, to be detected according to both a scan direction for the specimen scan unit and a direction approximately orthogonal to the scan direction; and a process unit constructed at least in part by hardware, to perform an addition process on scattering lights that are detected by plural pixels of the two dimensional plurality of pixels corresponding to a radial direction of the specimen, determining presence or absence of a defect based on scattering light treated by the addition process, and computing a size of the determined defect using at least one of the scattering lights corresponding to the determined defect.

7. The defect inspection apparatus according to claim 6, wherein an addition process of the process unit corrects a combination of scattering lights scattering approximately in the same direction from approximately the same area of the specimen based on a displacement amount measured by the specimen surface displacement measuring unit.

8. The defect inspection apparatus according to claim 6, further comprising:
    a display unit to display a position and a defect size detected on a surface of the specimen as determined to be defective by the process unit.

9. The defect inspection apparatus according to claim 6, wherein the specimen scan unit moves the specimen by translation and rotation to spirally scan a surface of the specimen.

10. The defect inspection apparatus according to claim 6, wherein the illumination condition includes light intensity, a beam diameter, a polarization state, and an incidence angle.

11. A defect inspection method performed by a processing unit constructed at least in part by hardware, the defect inspection method comprising:
    an illumination step of illuminating an area on surface of a specimen under a specified illumination condition;
    a specimen scan step of translating and rotating the specimen;
    a scattering light detection step of separating each of a plurality of scattering lights scattered in a plurality of directions from the illuminated area on the specimen into a two dimensional plurality of pixels to be detected, according to both a scan direction at the specimen scan step and a direction approximately orthogonal to the scan direction;
    a specimen surface displacement measuring step of measuring a displacement amount of a surface of the specimen in a height direction; and
    a process step of performing an addition process on scattering lights that are detected by plural pixels of the two dimensional plurality of pixels corresponding to a displacement amount measured at the specimen surface displacement measuring step, determining presence or absence of a defect based on scattering light treated by the addition process, and computing a size of the determined defect using at least one of the scattering lights corresponding to the determined defect.

12. A defect inspection apparatus comprising:
    an illumination unit to illuminate an area on surface of a specimen under a specified illumination condition;
    a specimen scan unit to translate and rotate the specimen;
    a scattering light detection unit to separate each of a plurality of scattering lights scattered in a plurality of directions from the illuminated area on the specimen into a two dimensional plurality of pixels to be detected, according to both a scan direction at the specimen scan step and a direction approximately orthogonal to the scan direction;
    a specimen surface displacement unit to measure a displacement amount of a surface of the specimen in a height direction; and
    a process unit constructed at least in part by hardware, to perform an addition process on scattering lights that are detected by plural pixels of the two dimensional plurality of pixels corresponding to a displacement amount measured at the specimen surface displacement measuring step, determine presence or absence of a defect based on scattering light treated by the addition process, and compute a size of the determined defect using at least one of the scattering lights corresponding to the determined defect.

* * * * *